US006120807A

United States Patent [19]
Gombotz et al.

[11] Patent Number: 6,120,807
[45] Date of Patent: Sep. 19, 2000

[54] PROLONGED RELEASE OF GM-CSF

[75] Inventors: Wayne Gombotz, Kirkland; Dean Pettit; Susan Pankey, both of Seattle, all of Wash.

[73] Assignee: Immunex Corporation, Seattle, Wash.

[21] Appl. No.: 09/185,213

[22] Filed: Nov. 3, 1998

Related U.S. Application Data

[62] Division of application No. 08/542,445, Oct. 12, 1995, Pat. No. 5,942,253.

[51] Int. Cl.[7] .................................................. A61K 9/50
[52] U.S. Cl. ............................................. 424/501; 424/502
[58] Field of Search ....................................... 424/501, 502

[56] References Cited

U.S. PATENT DOCUMENTS

| | | |
|---|---|---|
| 1,995,970 | 3/1935 | Dorough . |
| 2,675,945 | 4/1954 | Higgins . |
| 2,683,136 | 7/1954 | Higgins . |
| 2,703,316 | 3/1955 | Scneider . |
| 2,758,987 | 8/1956 | Salzberg et al. . |
| 2,951,828 | 9/1960 | Zeile . |
| 3,523,906 | 8/1970 | Vrancken . |
| 3,531,561 | 9/1970 | Trehu . |
| 3,737,337 | 6/1973 | Schnoring et al. . |
| 3,773,919 | 11/1973 | Boswell et al. . |
| 4,272,398 | 6/1981 | Jaffe . |
| 4,542,025 | 9/1985 | Tice et al. . |
| 4,767,628 | 8/1988 | Hutchinson et al. . |
| 4,849,228 | 7/1989 | Yamamoto et al. . |
| 4,897,268 | 1/1990 | Tice et al. . |
| 4,962,091 | 10/1990 | Eppstein et al. . |
| 5,000,886 | 3/1991 | Lawter et al. . |
| 5,078,996 | 1/1992 | Conlon et al. . |
| 5,192,741 | 3/1993 | Orsolini et al. . |
| 5,229,496 | 7/1993 | Deeley et al. . |
| 5,286,495 | 2/1994 | Hubbell et al. . |
| 5,391,485 | 2/1995 | Deeley et al. . |
| 5,393,870 | 2/1995 | Deeley et al. . |
| 5,410,016 | 4/1995 | Hubbell et al. . |
| 5,416,071 | 5/1995 | Igari et al. . |
| 5,478,564 | 12/1995 | Wantier et al. . |

OTHER PUBLICATIONS

Benita, et al, "Characterization of drug-loaded poly(d,l-lactide) microspheres," *J Pharm Sci.* 73(12):1721–4 (1984).

Braunstein, et al., "GM–CSF activates regenerative epidermal growth and stimulates keratinocyte proliferation in human skin in vivo," *J Invest Dermatol.* 103(4):601–4 (1994).

Grabstein, et al., "Regulation of antibody production in vitro by granulocyte–macrophage colony stimulating factor," *J Mol Cell Immunol.* 2(4):199–207 (1986).

(List continued on next page.)

*Primary Examiner*—Carlos A. Azpuru
*Attorney, Agent, or Firm*—Arnall Golden & Gregory, LLP

[57] ABSTRACT

Formulations for controlled, prolonged release of GM-CSF have been developed. These are based on solid microparticles formed of the combination of biodegradable, synthetic polymers such as poly(lactic acid) (PLA), poly(glycolic acid) (PGA), and copolymers thereof with excipients and drug loadings that yield zero order or first order release, or multiphasic release over a period of approximately three to twenty one days, preferably one week, when administered by injection. In the preferred embodiment, the microparticles are microspheres having diameters in the range of 10 to 60 microns, formed of a blend of PLGA having different molecular weights, most preferably 6,000, 30,000 and 41,000. Other embodiments hare been developed to alter the release kinetics or the manner in which the drug is distributed in vivo. For example, in some cases a polymer is selected which elicits a mild inflammatory reaction, for example, PLGA and polyanhydrides can act as chemoattractant, either due to the polymer itself or minor contaminants in the polymer, or polymers which are bioadhesive are used for transmucosal or oral delivery. In another embodiment, the GM-CSF is administered in a hydrogel which can be injected subcutaneous or at a specific site for controlled release. The microparticles or hydrogel are administered to the patient in an amount effect to stimulate proliferation of hematopoietic cells, especially white cells.

23 Claims, 6 Drawing Sheets

OTHER PUBLICATIONS

Lim, et al., "Microencapsulation of Living Cells and Tissues," *J. Pharm. Sci.* 70: 351–354 (1981).

Lu, et al., :Protein Release from Poly(lactic–co–glycolic acid) Microspheres: Protein Stability Problems, *J. Pharm. Sci. Technical* 49:13–19 (1995).

Hongkee Sah, et al., "The Influence of Biodegradable Microcapsule Formulations of a Controlled Release of a Protein," *J. Controlled Release* 30:201–211 (1994).

Mathiowitz, et al, "Morphology of Polyanhydride Microsphere Delivery Systems," *Scanning Microscopy* 4:329–340 (1990).

Mathiowitz, et al., "Polyanhydride Microspheres as Drug Carriers I. Hot–Melt Microencapsulation," *J. Controlled Release* 5:13–22 (1987).

Mathiowitz, et al., "Polyanhydride Microspheres as Drug Carriers II. Microencapsulation by Solvent Removal," *J. Appl. Polymer Sci.*:35: 755–774 (1988).

Mathiowitz, et al., "Novel Microcapsules for Delivery Systems," *Reactive Polymers* 6:275–283 (1987).

Morrissey, et al., "Granulocyte–Macrophage Colony––Stimulation Factor Augments the Primary Antibody response By Enhancing the Function of Antigen–Presenting Cells," *J. Immunology* 139: 1113–1119 (1987).

Salib, et al., "Utilization of Sodium Alginate in Drug Microencapsulation," *Pharmazeutische Industrie* 40(11A): 1230–1234 (1978).

PROLONGED RELEASE OF GM-CSF

RELATED APPLICATIONS

This is a divisional of application Ser. No. 08/542,445, filed Oct. 12, 1995, now U.S. Pat. No. 5,942,253.

BACKGROUND OF THE INVENTION

The present invention is generally in the area of controlled, prolonged release microsphere formulations for recombinant human granulocyte macrophage colony stimulating factor (GM-CSF).

GM-CSF, granulocyte macrophage colony stimulating factor, is a hematopoietic growth factor which promotes the proliferation and differentiation of hematopoietic progenitor cells. The cloned gene for GM-CSF has been expressed in bacteria, yeast and mammalian cells. The endogenous human protein is a monomeric glycoprotein with a molecular weight of about 22,000 daltons. GM-CSF produced in a yeast expression system is commercially available as Leukine® from Immunex Corporation, Seattle, Wash. It is a glycoprotein of 127 amino acids characterized by three primary molecular species having molecular masses of 19,500, 16,800, and 15,500 daltons.

Generally, GM-CSF is administered over a period of at least 6 to 7 days in order to obtain the optimal effect on the white blood cells. Under some circumstances, it is desirable to have a formulation which provides continuous, zero order or first order kinetic release of GM-CSF over a period of approximately one week. Moreover, sustained release formulation of GM-CSF may have advantageous therapeutic utilities not shared by standard liquid formulations. Sustained-release formulations of GM-CSF, however, are not currently available.

Controlled release formulations are well known for drug delivery. Both biodegradable and non-biodegradable polymers have been used to form microcapsules, microspheres or microparticles of various diameters, porosities, and drug loadings with the goal of obtaining release of the encapsulated drug over a period of time. Many formulations that have been developed have been designed for administration by injection, although the majority of controlled release formulations have enteric coatings or are formulations resistant to passage through the gastrointestinal tract that have been developed for oral administration.

It is difficult to achieve linear, controlled release using the standard formulations. Most formulations are designed either to provide very rapid release by diffusion and/or degradation of the polymer forming the microparticle or provide for a burst release followed by some kind of linear release which generally plateaus after a period of time. U.S. Pat. No. 5,192,741 to Orsolini, et al., is representative of the literature regarding the difficulties in obtaining controlled release from microspheres formed of poly(lactide-co-glycolides) (PLGAs). Similarly, Lu and Park *J. Pharm. Sci. Technical* 49, 13–19 (1995) describes the use of microcapsules, noting that one cannot obtain good release characteristics with microspheres and that protein stability in the microspheres is a problem. Since GM-CSF is an extremely potent compound where the effect may vary widely depending upon the given dosage, it may be advantageous in some circumstances to obtain a more linear release rather than a burst followed by a plateau of drug being released.

Representative of the many patents relating to controlled release are U.S. Pat. No. 4,767,628 to Hutchinson, disclosing multiphasic release of a peptide from a PLGA carrier. Blends of polymers are used is a large matrix delivery system to avoid multiphasic release. U.S. Pat. No. 4,897,268 to Tice, et al., discloses the use of different PLGAs in the same composition, but blends microspheres made of the different PLGAs to achieve linear release. U.S. Pat. No. 4,849,228 to Yamamoto, et al., claims PLGA microspheres having a very low monobasic acid content which allegedly have excellent release characteristics.

It is therefore an object of the present invention to provide a formulation encapsulating GM-CSF which provides for controlled, prolonged release with either zero order kinetics, first order release kinetics or multiphasic release kinetics over a period of greater than one day following administration to a patient by injection.

It is a further object of the present invention to provide a formulation for delivery of GM-CSF for administration orally, transmucosally, topically or by injection.

SUMMARY OF THE INVENTION

Formulations for controlled, prolonged release of GM-CSF have been developed. These are based on solid microparticles formed of the combination of biodegradable, synthetic polymers such as poly(lactic acid) (PLA), poly (glycolic acid) (PGA), and copolymers thereof with excipients and drug loadings that yield a sustained release over a period of one day to at least one week, when administered orally, transmucosally, topically or by injection. In the preferred embodiment, the microparticles have different diameters depending on their route of administration. Microparticles administered by injection have diameters sufficiently small to pass through a needle, in a size range of between 10 and 100 microns. Orally administered microparticles are less than 10 microns in diameter to facilitate uptake by the Peyer's patches in the small intestine.

Other embodiments have been developed to alter the release kinetics or the manner in which the drug is distributed in vivo. For example, in some cases a polymer is selected which elicits a mild inflammatory reaction, for example, PLGA and polyanhydrides, which can act as chemoattractant, either due to the polymer itself or minor contaminants in the polymer. In another embodiment, the GM-CSF is administered in a hydrogel which can be injected subcutaneous or at a specific site for controlled release.

The microparticles or hydrogel are administered to the patient in an amount effective to stimulate proliferation of hematopoietic cells, especially white cells. These are most preferably microspheres administered by injection.

Examples demonstrate the preparation of microparticles releasing GM-CSF over a prolonged period with zero order, first order, or multiphasic release kinetics. The type of release kinetics are determined for the particular clinical application. The data demonstrates that it is possible not only to achieve the desired release characteristics but also to retain extremely high levels of bioactivity of the encapsulated GM-CSF. Examples also demonstrate release from hydrogels.

DETAILED DESCRIPTION OF THE INVENTION

Figure 1A:
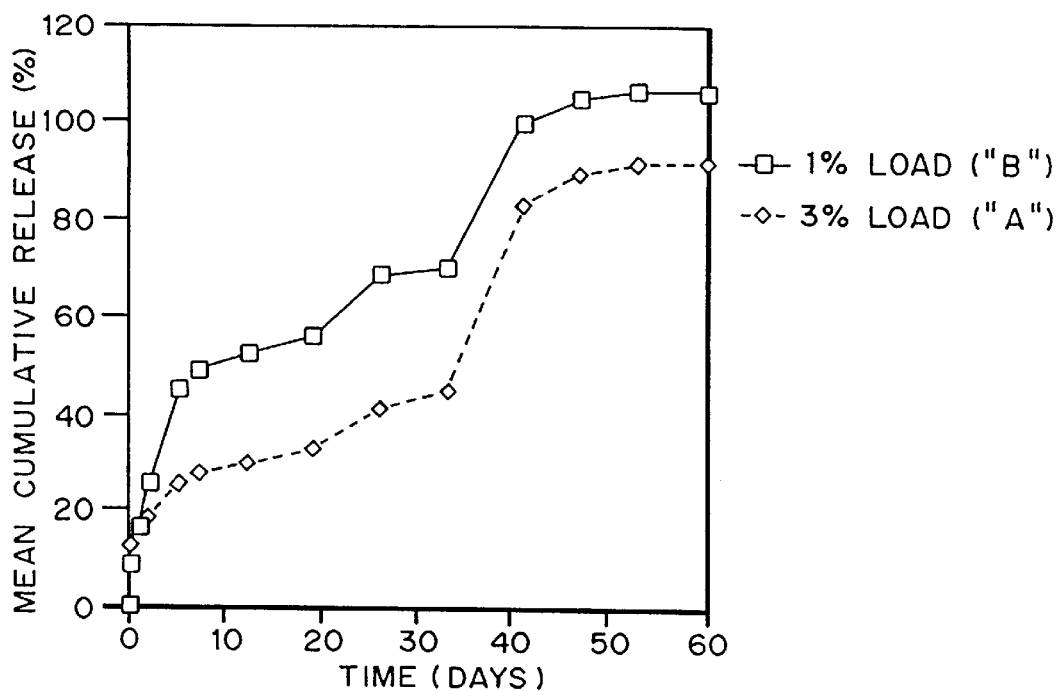
FIG. 1A is a graph of GM-CSF release, mean percent cumulative release in vitro over time (days) for a 1% load (squares) and 3% load (diamonds) in microspheres prepared by phase separation with a single PLGA copolymer.

There are many advantages for a controlled release formulation of GM-CSF. Among these are the convenience of a single injection for the patient and physician, avoidance of peaks and valleys in systemic GM-CSF concentration which is associated with repeated injections, the potential to reduce the overall dosage of GM-CSF, and the potential to enhance the pharmacological effects of GM-CSF. A controlled release formulation of GM-CSF also provides an opportunity to use GM-CSF in a manner not previously exploited, such as a vaccine adjuvant.

Controlled Release Formulations

As used herein, "sustained" or "extended" release of the GM-CSF can be continuous or discontinuous, linear or non-linear. This can be accomplished using one or more types of polymer compositions, drug loadings, inclusion of excipients or degradation enhancers, or other modifiers, administered alone, in combination or sequentially to produce the desired effect. Zero order or linear release is generally construed to mean that the amount of GM-CSF released over time remains relatively constant as a function of amount/unit time during the desired time frame, for example, six to seven days. Multi-phasic is generally construed to mean that release occurs in more than one "burst".

As used herein, "microparticles" refers to particles having a diameter of less than one mm, more typically less than 100 microns. Micropaticles can refer to microspheres, which are solid spherical microparticles, and microcapsules, which are spherical microparticles having a core of a different polymer, drug, or composition. Unless otherwise stated herein, microparticles refers to solid particles, not microcapsules.

Polymers for Formation of Microparticles

Many polymers have been used for controlled drug delivery. Polymers typically are thermoplastic synthetic polymers, such as ethylenevinyl acetate and poly(acrylic acid), which are generally viewed as non-biodegradable since they remain in relatively the same form over a period of at least two or three years following implantation in the body, and biodegradable polymers, such as poly(hydroxy acids) including polylactic acid, polyglycolic acid, and copolymers thereof, polyanhydrides, polyorthoesters, and certain types of protein and polysaccharide polymers. The term bioerodible or biodegrable, as used herein, means a polymer that dissolves or degrades within a period that is acceptable in the desired application (usually in vivo therapy), less than about five years and most preferably less than about one year, once exposed to a physiological solution of pH 6–8 at a temperature of between about 25° C. and 38° C.

A preferred polymer material is one which is biodegradable and which retains sufficient form to control release for a period following implantation of at least six to seven days. The poly (hydroxy acids), especially poly(lactic acid-co-glycolic acid) ("PLGA"), is a particularly preferred polymer since it has been used in the manufacture of degradable sutures for several decades. The polymer degrades by hydrolysis following exposure to the aqueous environment of the body. The polymer is hydrolyzed to yield lactic and glycolic acid monomers, which are normal byproducts of cellular metabolism. The rate of polymer disintegration can vary from several weeks to periods of greater than one year, depending on several factors including polymer molecular weight, ratio of lactide to glycolide monomers in the polymer chain, and stereoregularity of the monomer subunits (mixtures of L and D stereoisomers disrupt the polymer crystallinity enhancing polymer breakdown). Particularly useful results are obtained by blending PLGA having different molecular weights, and/or different ratios of lactide to glycolide. The molecular weight and monomer ratios can be optimized to tailor the release kinetics over a defined period of time. The higher molecular weights, result in polymer matrices which retain their structural integrity for longer periods of time; while lower molecular weights, result in both faster release and shorter matrix lives.

In a preferred embodiment described herein, the microspheres contain blends of at least two and more preferably three or more biodegradable polymers, preferably hydrolytically unstable polymers, most preferably poly(hydroxy acids) of different molecular weight and/or monomer ratio. In a preferred embodiment, three different molecular weight PLGAs are blended to form a composition that has linear release over a defined period of time, ranging from at least one day to about sixty days. In a more preferred embodiment to obtain release from about one to twenty-one days, the PLGAs have molecular weights between 1000 and 20,000, more preferably between 5,000 and 10,000, between 20,000 and 35,000, more preferably between 25,000 and 30,000, and between 35,000 and 70,000, more preferably 5000 and 10,000. In the most preferred embodiment for release over a period of about one week, PLGAs having molecular weights of about 6,000, 30,000, and 41,000 are combined.

PLA polymers are usually prepared from the cyclic esters of lactic acids. Both L(+) and D(−) forms of lactic acid can be used to prepare the PLA polymers, as well as the optically inactive DL-lactic acid mixture of D(-) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

Since it is desirable to target delivery of GM-CSF to white cells, particularly in the case where the GM-CSF is being used as an adjuvant, alone or in combination with antigen, the polymer may be selected based on properties other than just controlled release. For example, it is known that certain polymers are inflammatory and therefore attract leukocytes, macrophages and other "white" cells. Examples of "chemoattractant" polymers include the polyhydroxy acids (PL, PG, PLGAs), polyanhydrides, poly(ortho esters), and the polyphosphazenes.

In the case where the microparticles are intended for transmucosal or oral delivery, it may be desirable to select polymers which are bioadhesive. Examples of bioadhesive polymers include hydrophilic polymers, especially those containing carboxylic groups, such as poly(acrylic acid). Rapidly bioerodible polymers such as poly(lactide-co-glycolide), polyanhydrides, and polyorthoesters having carboxylic groups exposed on the external surface as their smooth surface erodes, are particularly useful. Representative natural polymers are proteins, such as zein, albumin, and collagen, and polysaccharides, such as cellulose, dextrans, and alginic acid. Other representative synthetic polymers include polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, celluloses including alkyl cellulose, hydroxyalkyl celluloses, cellulose ethers, cellulose esters, and nitrocelluloses, polymers of acrylic and methacrylic esters, poly(lactide-co-glycolide), polyanhydrides, polyorthoesters blends and copolymers thereof.

Polymers for Formation of Hydrogels

Other polymeric materials that may be useful include hydrogels such as the naturally occurring polysaccharides like alginate, as well as synthetic hydrogel materials such as some of the polyacrylic acids, polyphosphazenes, polyethylene glycol-PLGA copolymers and other synthetic biodegradable polymers which absorb up to 90% of the final weight of water.

The polymeric material which is mixed with GM-CSF for implantation into the body should form a hydrogel. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen. U.S. Pat. Nos. 5,286,495 and 5,410,016 to Hubbell, et al., describe useful materials for forming biocompatible hydrogels.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Calcium alginate and certain other polymers can form ionic hydrogels which are malleable can be used to encapsulate GM-CSF. Alginate can be ionically cross-linked with divalent cations, in water, at room temperature, to form a hydrogel matrix. The hydrogel is produced by cross-linking the anionic salt of alginic acid, a carbohydrate polymer isolated from seaweed, with divalent cations, whose strength increases with either increasing concentrations of calcium ions or alginate.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N^+$ —$C_6$— $^+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan. Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

These polymers are either commercially available or can be synthesized using methods known to those skilled in the art. See, for example *Concise Encyclopedia of Polymer Science* and *Polymeric Amines and Ammonium Salts*, E. Goethals, editor (Pergamen Press, Elmsford, N.Y. 1980).

GM-CSF

GM-CSF, granulocyte macrophage colony stimulating factor, is a hematopoietic growth factor which promotes the proliferation and differentiation of hematopoietic progenitor cells. The cloned gene for GM-CSF has been expressed in bacteria, yeast and mammalian cells. The endogenous protein is a monomeric glycoprotein with a molecular weight of about 22,000 daltons. The recombinant preparation expressed in bacterial cells is unglycosylated. GM-CSF produced in a yeast expression system is marketed as Leukine® by Immunex Corporation, Seattle, Wash. Leukine™ is sold in lyophilized form. It is a glycoprotein of 127 amino acids characterized by three primary molecular species having molecular masses of 19,500, 16,800, and 15,500 daltons.

GM-CSF is described in U.S. Pat. No. 5,078,996 to Conlon, et al. Analogs of GM-CSF are described in U.S. Pat. Nos. 5,229,496, 5,393,870, and 5,391,485 to Deeley, et al. In the preferred embodiment the GM-CSF is recombinant protein having a molecular weight of between approximately 14,000 and 20,000, made in yeast which hyperglycosylates the protein presumably limiting the amount of non-specific absorption observed with the protein. GM-CSF fusion proteins can also be used. Examples with GM-CSF fusion proteins include fusion proteins with IL-3 and other lymphokines or growth factors.

Preparation of Microparticles

Microspheres, or solid microparticles, can be prepared using any of a number of techniques known to those skilled in the art. GM-CSF appears to be unusually stable to processing, especially in the presence of organic solvents, which facilitates microparticle formation containing GM-CSF having very high levels of bioactivity, typically greater than 90% as compared to the GM-CSF prior to incorporation into the microparticles. Examples of methods for preparation include solvent evaporation, spray drying, solvent extraction and other methods known to those skilled in the art. As discussed above, hydrogels are typically formed by ionic crosslinking, by addition of ions or polyions, or photocrosslinking or other forms of chemical crosslinking.

Microsphere Preparation

Bioerodible microspheres can be prepared using any of the methods developed for making microspheres for drug delivery, for example, as described by Mathiowitz and Langer, *J. Controlled Release* 5, 13–22 (1987); Mathiowitz, et al., *Reactive Polymers* 6, 275–283 (1987); and Mathiowitz, et al., *J. Appl. Polymer Sci.* 35, 755–774 (1988), the teachings of which are incorporated herein. The selection of the method depends on the polymer selection, the size, external morphology, and crystallinity that is desired, as described, for example, by Mathiowitz, et al., *Scanning Microscopy* 4, 329–340 (1990); Mathiowitz, et al., *J. Appl. Polymer Sci.* 45, 125–134 (1992); and Benita, et al., *J. Pharmn. Sci.* 73, 1721–1724 (1984), the teachings of which are incorporated herein. Methods include solvent evaporation, phase separation, spray drying, and hot melt encapsulation. U.S. Pat. Nos. 3,773,919; 3,737,337; and 3,523,906 are representative of methods for making microspheres.

A preferred method is described in U.S. Pat. No. 5,000,886 to Lawter, et al., the teachings of which are incorporated herein. The GM-CSF is dispersed in an aqueous solution which is then mixed with an organic solution of the polymer. The dispersion is added to a non-solvent for the polymer and the GM-CSF, then the microparticles hardened by extraction of the polymer solvent into a volatile silicone fluid.

In solvent evaporation, described for example, in Mathiowitz, et al., (1990), Benita, and U.S. Pat. No. 4,272,398 to Jaffe, the polymer is dissolved in a volatile organic solvent. The GM-CSF, either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres.

In general, the polymer can be dissolved in methylene chloride. Several different polymer concentrations can be used, for example, between 0.01 and 0.50 g/ml. After loading the solution with GM-CSF, the solution is suspended in 200 ml of vigorously stirring distilled water containing 1% (w/v) poly(vinyl alcohol) (Sigma Chemical Co., St. Louis, Mo.). After four hours of stirring, the organic solvent will have evaporated from the polymer, and the resulting microspheres will be washed with water and dried overnight in a lyophilizer.

Microspheres with different sizes (1–1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

Solvent removal is particularly useful with polyanhydrides. In this method, the drug is dispersed or dissolved in a solution of a selected polymer in a volatile organic solvent like methylene chloride. The mixture is then suspended in oil, such as silicone oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used.

In spray drying, the polymer is dissolved in methylene chloride (0.04 g/ml). A known amount of active drug is suspended (if insoluble) or co-dissolved (if soluble) in the polymer solution. The solution or the dispersion is then spray-dried. Microspheres ranging in diameter between one and ten microns can be obtained with a morphology which depends on the selection of polymer.

Hydrogel microparticles made of gel-type polymers such as alginate or polyphosphazenes or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microparticles fall into a slowly stirring, ionic hardening bath, as described, for example, by Salib, et al., *Pharmazeutische Industrie* 40–11A, 1230 (1978), the teachings of which are incorporated herein. The advantage of this system is the ability to further modify the surface of the microparticles by coating them with polycationic polymers such as polylysine, after fabrication, for example, as described by Lim, et al., *J. Pharm. Sci.* 70, 351–354 (1981). As described by Lim, et al., in the case of alginate, a hydrogel can be formed by ionically crosslinking the alginate with calcium ions, then crosslinking the outer surface of the microparticle with a polycation such as polylysine, after fabrication. The microsphere particle size are controlled using various size extruders, polymer flow rates and gas flow rates.

Chitosan microparticles can be prepared by dissolving the polymer in acidic solution and crosslinking with tripolyphosphate. For example, carboxymethylcellulose (CMC) microsphere are prepared by dissolving the polymer in an acid solution and precipitating the microparticles with lead ions. Alginate/polyethylene imide (PEI) can be prepared to reduce the amount of carboxyl groups on the alginate microparticles Loading of GM-CSF The range of loading of the GM-CSF to be delivered is typically between about 0.001% and 10%, by weight. GM-CSF can be incorporated into a polymeric matrix at a ratio of between 0.001% by weight up to 10% by weight. In a preferred embodiment, GM-CSF is incorporated into PLGA blends to 2% by weight.

Loading is dependent on the disorder to be treated as well as the time period over which the GM-CSF is to be released. Lower dosages are required for use as a vaccine adjuvant, in the range of 0.001 to 0.1%. Microparticles for treatment of a severe infection would typically be delivered in microparticles with 2% by weight drug loading.

Additives to Microparticles Altering Release

Polymer hydrolysis is accelerated at acidic or basic pH's and thus the inclusion of acidic or basic excipients can be used to modulate the polymer erosion rate. The excipients can be added as particulates, can be mixed with the incorporated GM-CSF or can be dissolved within the polymer.

Degradation enhancers are based on weight relative to the polymer weight. They can be added to the protein phase, added as a separate phase (i.e., as particulates) or can be codissolved in the polymer phase depending on the compound. In all cases the amount should be between 0.1 and thirty percent (w/w, polymer). Types of degradation enhancers include inorganic acids such as ammonium sulfate and ammonium chloride, organic acids such as citric acid, benzoic acids, heparin, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween™ and Pluronic™.

Pore forming agents are used to add microstructure to the matrices (i.e., water soluble compounds such as inorganic salts and sugars). They are added as particulates. The range should be between one and thirty percent (w/w, polymer).

Excipients can be also added to the GM-CSF to maintain its potency depending on the duration of release. Stabilizers include carbohydrates, amino acids, fatty acids, and surfactants and are known to those skilled in the art. In addition, excipients which modify the solubility of GM-CSF such as salts, complexing agents (albumin, protamine) can be used to control the release rate of the protein from the microparticles.

Stabilizers for the GM-CSF are based on the ratio by weight of stabilizer to the GM-CSF on a weight basis. Examples include carbohydrate such as sucrose, lactose, mannitol, dextran, and heparin, proteins such as albumin and protamine, amino acids such as arginine, glycine, and threonine, surfactants such as Tween™ and Pluronic™, salts such as calcium chloride and sodium phosphate, and lipids such as fatty acids, phospholipids, and bile salts.

The ratios are generally 1:10 to 4:1, carbohydrate to protein, amino acids to protein, protein stabilizer to protein, and salts to protein; 1:1000 to 1:20, surfactant to protein; and 1:20 to 4:1, lipids to protein.

Clinical Indications to be Treated

Systemic Delivery for Proliferation of Cells

GM-CSF is approved for treatment of patients requiring increased proliferation of white blood cells. Data indicates that GM-CSF is also useful as a vaccine adjuvant Morrissey, et al., *J. Immunology* 139, 1113–1119 (1987). GM-CSF microparticles can also be used to treat patients prone to infection such as those undergoing high risk bowel surgery, trauma victims and individuals with HIV. The protocols and clinical efficacy of GM-CSF is well known to those skilled in the art. As described herein, the protocols are modified to reflect the changes in delivery rates and dosages resulting from the release profiles from microparticles or hydrogels, as appropriate.

In vitro data regarding release profiles for GM-CSF, as well as efficacy, appears to be predictive, although not identical, of in vivo data. As demonstrated by the following examples, Rhesus monkey data show maximum increases in leucocyte numbers within four days following administration of GM-CSF, while in vitro results demonstrated that six to seven days are required for complete release of the incorporated GM-CSF. The advantage of using GM-CSF is that the protein is itself extremely stable, with at least 60%, in many cases 90 to 100%, of the bioactivity being retained after incorporation into microparticles using any one of several processes.

Local Administration as Adjuvant

Enhanced vaccine response can be obtained through the use of GM-CSF alone, but is more preferably obtained through a selection of the polymer in combination with the controlled release of the GM-CSF. It is known that certain polymers serve as chemoattractants for white cells. PLGA is mildly inflammatory, as are polyanhydrides and polyorthoesters. Through the selection of the chemoattractant polymer as the matrix for GM-CSF, in a form yielding controlled release over a period of approximately one week, maximum vaccine enhancement can be obtained. In this embodiment, release can be from polymeric matrices in a variety of forms, not just microparticles or hydrogels. The GM-CSF and polymer may even act synergistically to enhance the adjuvant effect of the GM-CSF, as well as targeting of the GM-CSF to the white cells.

The GM-CSF can also be injected with a tumor antigen or tumor cells that express antigens or their surfaces for use as a tumor vaccine.

Topical or Transmucosal Administration

The hydrogel formulations are particularly useful for topical applications. For example, GM-CSF has been shown by Braunstein et al., *J. Invest. Dermatol* 103, 601–604 (1994) to stimulate keratinocyte proliferation in human skin and could thus be utilized as a topical wound healing agent. Mucosal delivery of GM-CSF microparticles could also be efficacious in the stimulation of mucosal immunity since the protein has been shown to play a role in antibody production (Grabstein, et al., *J. Mol. Cell. Immunol.* 2, 199–207 (1986)).

Administration of the GM-CSF Microparticles

In the preferred embodiment for stimulation of proliferation of hematopoietic progenitor cells, GM-CSF is administered incorporated in microparticles which degrade over a period of 1 of 2 months. The microparticles preferably range in size from 10 to 60 microns, with an average of 35 microns in diameter, and are injected simultaneously with the aid of a suspension media. In one embodiment, the suspension media consists of 3% methyl cellulose, 4% mannitol, and 0.1% Tween™ 80, using a 22 gauge needle. In another embodiment the 3% methylcellulose is replaced by 1% carboxy methylcellulose. One ml of viscous suspension media is required to suspend 100 milligrams of microparticles which contain enough GM-CSF to deliver 125 micrograms/$m^2$/day over a period of 7 days. Larger doses may be achieved by injecting more microparticles. For example, a 250 microgram/$m^2$/day dose would require two 1 ml injections, each containing 100 mg of microparticles.

The present invention will be further understood by reference to the following non-limiting examples.

EXAMPLE 1

Preparation of Microspheres Using Phase Separation Process.

A. Lot #14223-133, Sample "A"

The encapsulating polymer was a poly(glycolide-co-d,1 lactide) having an inherent viscosity of 0.43 dL/g (as determined in a 0.5% w/v hexafluoroisopropanol solution at 30° C.), and a glycolide to lactide ratio of 45:55. It was prepared with glycolic acid as the initiator and stannous chloride dihydrate as the catalyst. The distribution of lactoyl and glycoyl groups within the copolymer was shown to be random by C13 NMR and solubility measurements. The residual lactide content was reduced by vacuum stripping. The encapsulating polymer solution was prepared by adding 100 g of the polymer to 900 g of methylene chloride, and stirring the mixture until the polymer dissolved.

0.978 ml of a GM-CSF solution (at 63.3 mg/ml in 100 mM tris buffer) was added to a 20 g portion of the encapsulating polymer solution. The mixture was stirred with a homogenizer using a 10-mm head at 10,000 RPM for 2 minutes to create a water-in-oil (W/O) emulsion.

18.0 g of Dow Corning® 360 Fluid (polydimethylsiloxane) was added to the W/O emulsion, and the mixture was homogenized at 10,000 RPM for 2 minutes. The mixture was then added to 2.4 kg of Dow Corning® 244 Fluid (octamethylcyclotetrasiloxane) under stirring at 750 RPM to harden the microspheres. Stirring was continued for 90 minutes. Microspheres were collected with a strainer fitted with a 1 μm stainless steel screen, then dried under vacuum.

Particle size distribution was analyzed with a Malvern 2600 Particle Sizer. Approximately 50 mg of microspheres were suspended in about 10 ml of Dow Corning® 244 Fluid, and was sonicated for 2 minutes to fully disperse the microspheres. A few drops of this suspension were then added to the optical cell which contained Dow Corning® 244 Fluid. The particle size distribution was then measured. The sample had a volume median diameter of 66.7 μm, 10% of the microspheres were under 24.1 μm, 90% of the microspheres were under 118.6 μm.

B. Lot #14223-134, Sample "B"

The encapsulating polymer and its solution in methylene chloride were the same as described in "A".

0.320 ml of a GM-CSF solution (at 63.3 mg/ml in 100 rnM tris buffer) was added to a 20 g portion of the encapsulating polymer solution. The mixture was stirred with a homogenizer using a 10-mm head at 10,000 RPM for 2 minutes to create a water-in-oil (W/O) emulsion.

18.0 g of Dow Corning® 360 Fluid (polydimethylsiloxane) were added to the W/O emulsion, and the mixture was homogenized at 10,000 RPM for 2 minutes. The mixture was then added to 2.4 kg of Dow Corning® 244 Fluid (octamethylcyclotetrasiloxane) under stirring for 90 minutes at 750 RPM to harden the microspheres. Microspheres were collected, dried and particle size distribution analyzed as described in "A". The sample had a volume median diameter of 43.8 μm, 10% of the microspheres were under 7.0 μm, 90% of the microspheres were under 77.9 μm.

As shown in FIG. 1A, samples "A" and "B" demonstrate that PLGA microspheres can be fabricated to release GM-CSF in a triphasic manner. In the first phase, the protein is released continuously over approximately 5 days. This phase is followed by a period of minimal GM-CSF release until day 35. At this time another pulse of GM-CSF is released from the system. The duration of each phase can be controlled by the type of polymers used to prepare the microspheres.

C. Lot #9663-96A. Sample "B4"

The encapsulating polymer was a 60:20:20 mixture of 1) a poly(glycolide-co-d,1 lactide) having a glycolide to lactide ratio of 47:53 and an inherent viscosity of 0.72 dL/g as determined in a 0.5% w/v hexafluoroiisopropanol solution at 30° C. (polymer I), 2) a poly(glycolide-co-d,1 lactide) having a glycolide to lactide ration of 50:50 and an inherent viscosity of 0.33 dL/g as determined in a 0.1% w/v chloroform solution at 25° C. (polymer II), and 3) a poly(d,1 lactide) with an average molecular weight of 1938 as determined by end group titration (polymer III). Polymer II and polymer III were reprecipitated before use. The encapsulating polymer solution was prepared by adding 1.20 g of polymer I, 0.40 g of polymer II, and 0.40 g of polymer III to 18.00 g of methylene chloride and stirring the mixture until the polymers dissolved.

0.481 ml of a GM-CSF solution at 84.8 mg/ml in 100 mM tris buffer) was added to the encapsulating polymer solution, homogenized with a 20-mm head at 10,000 RPM for 60 seconds to created a water-in-oil (W/O) emulsion.

The beaker containing the W/O emulsion was placed under a mixer equipped with a 3-blade Teflon stirrer and stirred at 1000 RPM. 20 ml of Dow Corning® 360 Fluid was added to the W/O emulsion while it was being stirred at 1000 RPM over a 1-minute period of time using a syringe pump.

The mixture was then added to 2.0 kg of Dow Corning® 244 Fluid under stirring for 90 minutes at 400 RPM to harden the microspheres.

Microspheres were collected, dried and Particle size distribution was analyzed as described above. The sample had a volume median diameter of 31.8 μm, 10% were under 14.1 μm and 90% of the microspheres were under 52.2 μm.

D. Lot #9663-135C, Sample "04,"

The encapsulating polymer was a 60:20:20 mixture of: 1) a poly(glycolide-co-d,1 lactide) having a glycolide to lactide ratio of 47:53 and an inherent viscosity of 0.72 dL/g as determined in a 0.5% w/v hexafluoroisopropanol solution at 30° C. (polymer I), 2) a poly(glycolide-co-d,1 lactide) having a glycolide to lactide ratio of 50:50 and an inherent viscosity of 0.33 dL/g as determined in a 0.1% w/v chloroform solution at 25° C. (polymer II), and 3) a poly(d,1 lactide) with an average molecular weight of 1938 as determined by end group titration (polymer III). Polymer II and polymer III were reprecipitated before use. The encapsulating polymer solution was prepared by adding 1.20 g of polymer I, 0.40 g of polymer II, and 0.40 g of polymer III to 18.00 g of methylene chloride and stirring the mixture until the polymers dissolved.

0.462 ml of a GM-CSF solution (at 88.4 mg/ml in 100 mM tris buffer) was added to the encapsulating polymer solution, homogenized with a 20-mm head at 10,000 RPM for 60 seconds to create a water-in-oil (W/O) emulsion. The W/O emulsion was stirred at 1000 RPM. 20 ml of Dow Corning® 360 Fluid was added to the W/O emulsion while it was being stirred over a 1-minute period of time using a syringe pump. The mixture was then added to 2.0 kg of Dow Corning® 244 Fluid under stirring at 400 RPM for 90 minutes to harden the microspheres.

Microspheres were collected, dried and particle size distribution was analyzed as described above. The sample had a volume median diameter of 39.5 μm, 10% of the microspheres were under 14.9 μm, and 90% of the microspheres were under 65.1 μm.

E. Lot #9490-168, Sample "V4." Aseptic Process

Microspheres were prepared aseptically as follows. Glassware, mixer shafts and heads, and stainless steel vessels were autoclaved prior to use.

The encapsulating polymer was a 60:20:20 mixture of 1) poly(glycolide-co-d,1 lactide) having a glycolide to lactide ratio of 47:53 and an inherent viscosity of 0.72 dL/g as determined in a 0.5% w/v hexafluoroisopropanol solution at 30° C. (polymer I), 2) a poly(glycolide-co-d,1 lactide) having a glycolide to lactide ratio of 50:50 and an inherent viscosity of 0.33 dL/g as determined in a 0. 1% w/v chloroform solution at 25° C. (polymer II), and 3) a poly(d,1 lactide) with an average molecular weight of 1938 as determined by end group titration (polymer III). Polymer II and polymer III were reprecipitated before use. The encapsulating polymer solution was prepared by adding 3.00 g of polymer I, 1.00 g of polymer II, and 1.00 g of polymer III to 45.00 g of methylene chloride and stirring the mixture until the polymers dissolved. 20.00 g of this solution was filtered through a glass fiber prefilter and a 0.45 μm Teflon filter for microencapsulation.

Approximately 100 g of Dow Corning® 360 Fluid was heated at 160° C. for 1 hour in a glass beaker covered with aluminum foil, then cooled to room temperature.

2.0 kg of Dow Corning® 244 Fluid was filtered through a "Millipak™20" 0.22 μm filter into the hardening vessel.

0.485 ml of a GM-CSF solution (at 87.3 mg/ml in 100 mM tris buffer, filtered through a 0.2 μm filter) was added to the 20 grams of filtered encapsulating polymer solution, stirred with a homogenizer using a 20-mm head at 10,000 RPM for 60 seconds to create a water-in-oil (W/O) emulsion.

The beaker containing the W/O emulsion was placed under a mixer equipped with a 3-blade Teflon stirrer and stirred at 1000 RPM. 20 ml of the heat-treated Dow Corning® 360 Fluid was added to the W/O emulsion while it was being stirred at 1000 RPM over a 1 minute period of time using a syringe pump.

The mixture was then added to the 2.0 kg of filtered Dow Corning® 244 Fluid under stirring at 400 RPM to harden the microspheres. Stirring was continued for 90 minutes.

Microspheres were collected, dried and the particle size distribution was determined with a Malvern 2600 Particle Sizer. The particle size distribution was then measured. The sample had a volume median diameter of 32.5 μm, 10% of the microspheres were under 14.7 μm, and 90% of the microspheres were under 54.8 μm.

EXAMPLE 2

Analysis of GM-CSF Incorporated into Microspheres Using Reversed Phase High Performance Liquid Chromatography.

GM-CSF was first extracted from microspheres using acetic acid, methylene chloride and phosphate buffered saline. A control consisting of blank microspheres with freshly added stock GM-CSF was concurrently extracted. The extracts were then evaluated by RP-HPLC for glycoform distribution.

Recombinant human (rhu) GM-CSF glycosylated variants are measured using high performance liquid chromatography (HPLC). The column is a C18 10 micron, 300 angstrom column (4.6 mm×25 cm) from Vydac. The glycoforms of GM-CSF can be resolved in this method using a mobile phase gradient of 25 to 65% 0.1% trifluoroacetic acid (TFA)/acetonitrile in 0.1% TFA/water with constant 200 mM NaCl.

Results show that the GM-CSF glycoform distribution of the control is not altered due to the extraction protocol and the RP-HPLC profile of GM-CSF incorporated into microspheres remains unchanged.

EXAMPLE 3

GM-CSF Release Kinetics from Microsphere Preparations.

Release kinetics of GM-CSF microspheres were analyzed using the following methods. Microsphere lots were stored in their original containers at 2–8° C. The in vitro release studies were initiated within a few days of preparation. Studies were set up in duplicate for screening and in triplicate for increased confidence in accuracy and precision. The release buffer was phosphate buffered saline (PBS, 12 mM sodium phosphate, 3.7 mM potassium phosphate, 150 mM sodium chloride, pH 7.0, 0.22 μm filtered) containing 0.02% sodium azide as preservative, although it is recommended to leave out the azide and handle the release study as aseptically as possible when bioactivity analysis of the released GM-CSF is planned. Collection time intervals in a study may include times at 2, 6, 24, 48, 72 hrs, 5, 7, 10, and 14 days.

To set up an in vitro release assay, approximately 50 to 75 mg of microspheres were placed in the 9 mm ID×13 mm OD×5 mm teflon spacer which is within the teflon jacket of the device. The spacer was anchored at both ends with 13 mm diameter, 10 μm mesh stainless steel screens which allow circulation of release buffer through the microspheres.

The loaded device was placed into a wide, 30 ml polypropylene test tube with 6 ml release buffer. The open tubes containing the loaded device and release buffer were covered with loose caps or Kimwipes® secured with rubber bands and placed in a vacuum desiccator. Exposure to vacuum for approximately 2 hours helps remove any trapped air bubbles and promotes initial wetting of the microspheres. The tubes were then capped and incubated at 37° C. on an orbital shaker set at 100 rpm.

At appropriate time intervals the release buffer was retrieved by decanting into preweighed, labelled 15 ml polypropylene test tubes. The volume obtained was determined by weight (ml=g, approximately). The device, with an addition of fresh release buffer (6 ml), was then returned to the orbital shaker at 37° C.

The microsphere release samples were evaluated by the Bio-Rad Total Protein Assay to quantify the release of GM-CSF. A total protein assay can be used since there is no other protein present.

Figure 1B:
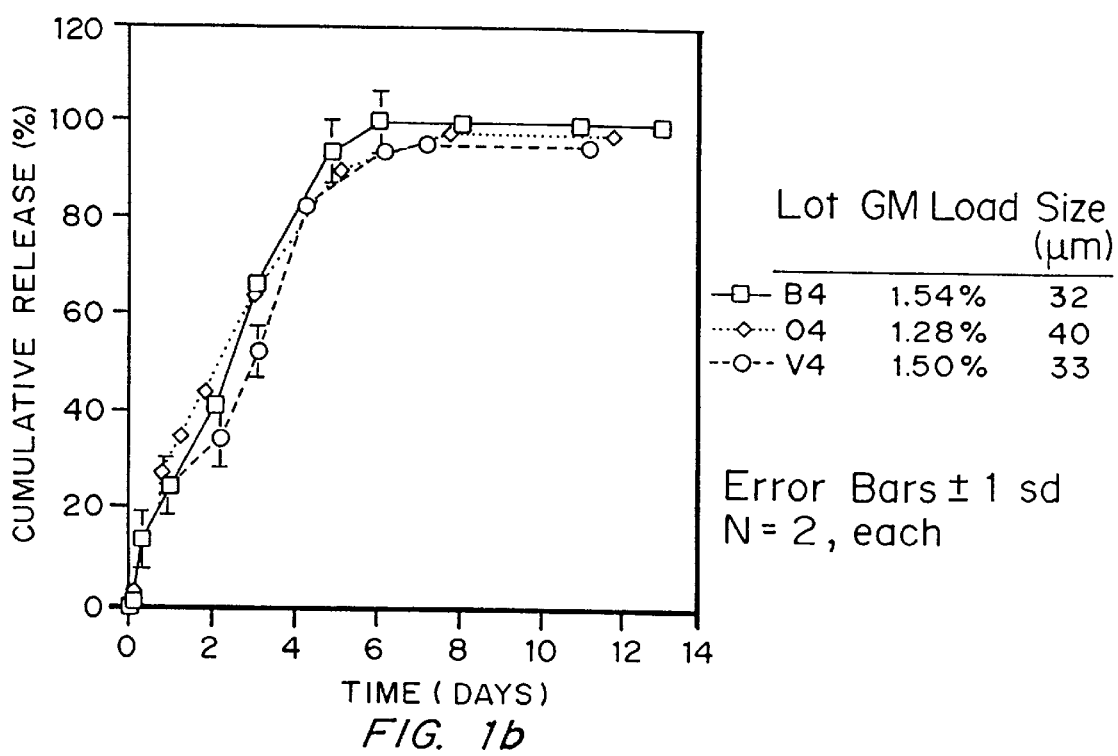
FIG. 1B is a graph of GM-CSF release, mean percent cumulative release in vitro over time (days) for a 1.54% load (squares, lot B4), 1.28% load (diamonds, lot O4) and 1.5% load (circles, lot V4) in microspheres prepared by phase separation using a blend of PLA and PLGA polymers.
Figure 3A:
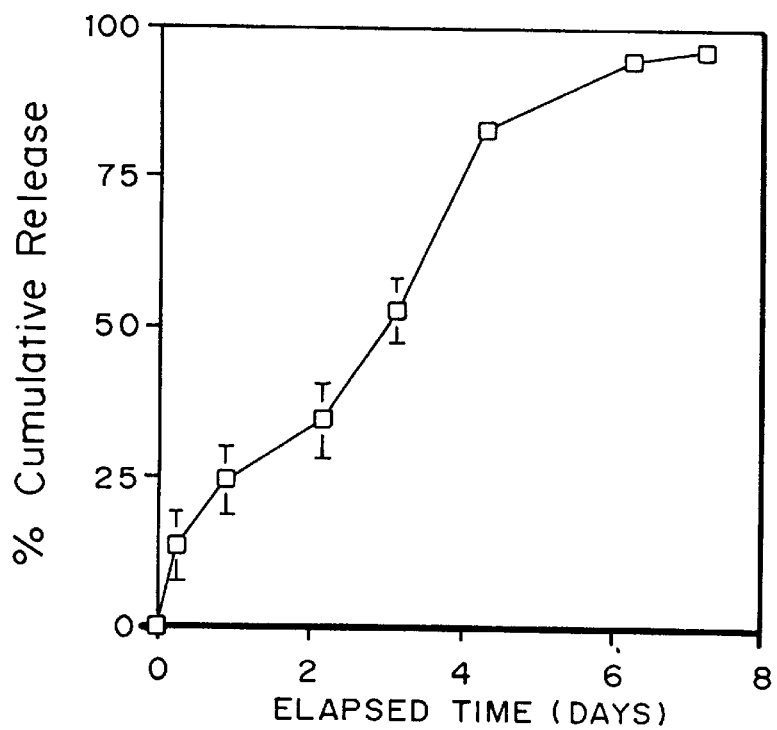
FIG. 3A is a graph of GM-CSF release, mean percent cumulative release in vitro over time (days) for lot V4 microspheres prepared by phase separation using a blend of two PLGAs of different molecular weight and a PLA.
Figure 3B:
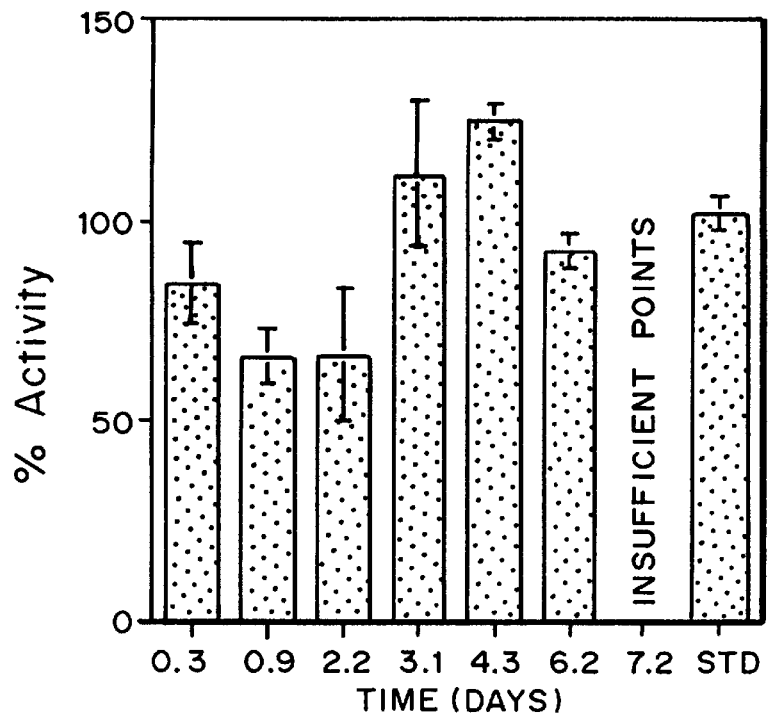
FIG. 3B is a graph of TF-1 bioactivity of lot V4 release samples, percent activity at discrete time points (days).

The results of the release kinetics analysis are shown in FIGS. 1B and 3A. Samples "B4", "04" and "V4", prepared in Example 1, show that PLGA microspheres can be fabricated to continuously release GM-CSF over a period of approximately 6 days. The release is linear over this time and approaches zero order. Furthermore, the GM-CSF is released with essentially complete retention of bioactivity as shown in FIG. 3B (given the standard deviation of the bioassay, the released GM-CSF can be considered completely active.) These examples also show that the microsphere fabrication process is highly reproducible as evidenced by the very similar GM-CSF release profiles generated from the three preparations. cl EXAMPLE 4

In Vivo Release Profile of huGM-CSF in a Murine Model

A. Lot #9402-94, Sample "O"

Microspheres were prepared aseptically as follows:

Glassware, mixer shafts and heads, and stainless steel vessels were autoclaved prior to use. 4.0 kg of Dow Corningg 244 Fluid (octamethylcyclotetrasiloxane) was filtered through a "Millipak® 40" 0.22 $\mu$m filter into the hardening vessel. Approximately 100 g of Dow Corning™ 360 Fluid (polydimethylsiloxane, 350 centistrokes) was heated at 160° C. for 80 minutes in a glass beaker covered with aluminum foil, then cooled to room temperature.

A 40-gram portion of a 10% poly(glycolide-co-d,1 lactide) solution in methylene chloride was filtered through a polyvinylidene fluoride 0.22 $\mu$m filter for microencapsulation. The polymer had an inherent viscosity of 0.43 dL/g as determined in a 0.5% w/v hexafluoroisopropanol solution at 30° C., and a glycolide to lactide ratio of 45:55. It was prepared with glycolic acid as the initiator and stannous chloride dihydrate as the catalyst. The distribution of lactoyl and glycoyl groups within the copolymer was shown to be random by C13 NMR and solubility measurements. The residual lactide content was reduced by vacuum stripping.

0.664 ml of a GM-CSF solution (about 63.1 mg/ml in 100 mM tris buffer, filtered through a 0.2 $\mu$m filter) was added to the 40 grams of filtered polymer solution, stirred with a homogenizer using a 20-mm head at 10,000 RPM for 60 seconds to create a water-in-oil (W/O) emulsion. 36 ml of the heat-treated Dow Corning® 360 Fluid was added to the W/O emulsion, and the mixture was homogenized at 5000 RPM for 90 seconds. The mixture was then added to the 4.0 kg of filtered Dow Corning® 244 Fluid under stirring at 500 RPM to harden the microspheres. Stirring was continued for 1 hour. Microspheres were collected, dried and particle size distribution analyzed as described above. The sample had a volume median diameter of 56.0 $\mu$m, 10% of the microspheres were under 26.3 $\mu$m, 90% of the microspheres were under 91.6 $\mu$m.

Figure 2A:
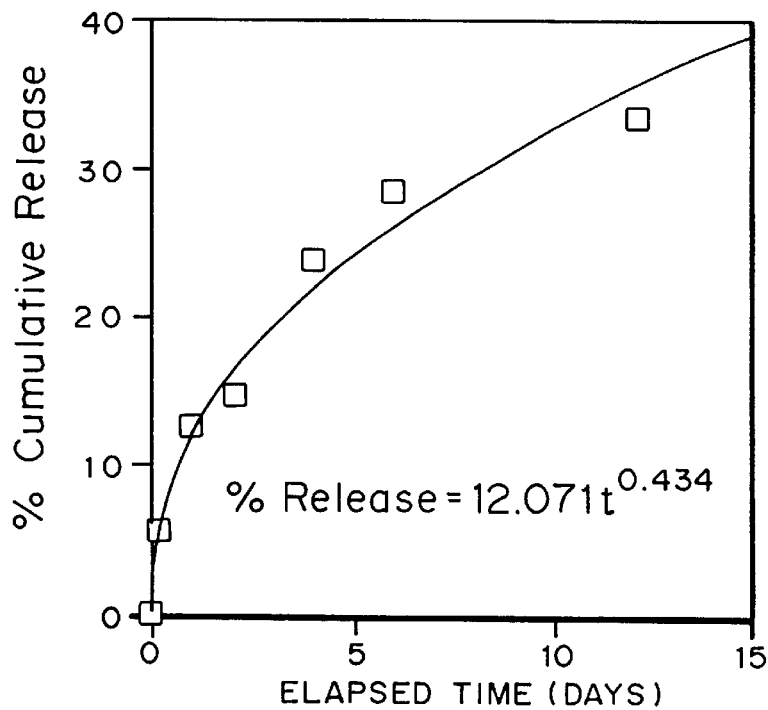
FIG. 2A is a graph of in vitro release kinetics for "Lot O" microspheres prepared by phase separation of a single molecular weight PLGA, showing GM-CSF release as percent cumulative release in vitro over time (days).

The microspheres were first analyzed for in vitro release characteristics to ensure continuous release of huGM-CSF over a period of greater than 7 days (FIG. 2A). The microspheres were then weighed and loaded into 3 cc syringes with 50 mg of microspheres/syringe. The injection vehicle for the microspheres was an aqueous solution of low viscosity grade methyl cellulose, containing 3% (w/w) methyl cellulose, 0.1% Tween 80, and 4% mannitol (final osmolality=292 mOsm/kg). Vials were loaded with 1 g each of sterile filtered injection vehicle solution. For injection, an 18-gauge needle was attached to an empty 3 cc syringe and used to withdraw 0.5–0.6 ml of injection vehicle. The needle was then removed from the syringe and the syringe containing the vehicle was attached to a syringe containing microspheres through a "syringe connector". Mixing was achieved by pushing the syringes back-and-forth 25 times in each direction. The empty syringe and the syringe connector were then removed. A 22 gauge needle was then attached to the syringe with suspended microspheres ready for injection.

Release Studies in Mice

Release studies were conducted on mice as follows. Male B6 mice (6 weeks old) were obtained from Jackson Laboratories (Bar Harbor, Me.) and were housed in the Immunex animal laboratory facility for an additional 10 weeks prior to initiating the study. Seventeen groups of mice were used in the study, with three mice used per group. For the test group 50 mg of microspheres containing 500 $\mu$g of huGM-CSF (1% by wt) were injected subcutaneously in 0.5 ml of the methyl cellulose injection vehicle. Groups of mice receiving these injections were sacrificed at intervals of 1, 2, 6, 24 hr, 3, 5, 7, and 9 days. As a negative control, one group of mice was sacrificed without receiving huGM-CSF in any form. As a final control a bolus of huGM-CSF was injected subcutaneously at a dose of either 500 or 50 $\mu$g of huGM-CSF. The 500 $\mu$g dose represented the entire amount of huGM-CSF contained in a 50 mg injection of microspheres, and the 50 $\mu$g dose represented an approximation of the amount of huGM-CSF released by 50 mg of microspheres over a period of 1 day in vitro. Groups of mice receiving bolus injections were sacrificed at intervals of 1, 2, 6, and 24 hr post-injection.

Following sacrifice of the mice, blood samples were obtained and allowed to clot at 4° C. The sera was then harvested and the clot was discarded. Remaining cellular debris was removed by centrifugation, and the serum samples were then frozen at −70° C. until further analysis.

TABLE 1

In Vivo Microsphere Release Study Outline

| Group | Description | Post-Injection Sacrifice Time |
|---|---|---|
| 1 | no injection, negative control | 0 hr |
| 2 | 500 $\mu$g huGM-CSF bolus injection | 1 hr |
| 3 | 50 $\mu$g huGM-CSF bolus injection | 1 hr |
| 4 | 50 mg microspheres injected | 1 hr |
| 5 | 500 $\mu$g huGM-CSF bolus injection | 2 hr |
| 6 | 50 $\mu$g huGM-CSF bolus injection | 2 hr |
| 7 | 50 mg microspheres injected | 2 hr |
| 8 | 500 $\mu$g huGM-CSF bolus injection | 6 hr |
| 9 | 50 $\mu$g huGM-CSF bolus injection | 6 hr |
| 10 | 50 mg microspheres injected | 6 hr |

TABLE 1-continued

In Vivo Microsphere Release Study Outline

| Group | Description | Post-Injection Sacrifice Time |
|---|---|---|
| 11 | 500 μg huGM-CSF bolus injection | 24 hr |
| 12 | 50 μg huGM-CSF bolus injection | 24 hr |
| 13 | 50 mg microspheres injected | 24 hr |
| 14 | 50 mg microspheres injected | 72 hr (3 day) |
| 15 | 50 mg microspheres injected | 120 hr (5 day) |
| 16 | 50 mg microspheres injected | 168 hr (7 day) |
| 17 | 50 mg microspheres injected | 216 hr (9 day) |

Serum samples were thawed and analyzed by ELISA for determination of huGM-CSF concentrations. The GM-CSF enzyme linked immunoassay (EIA) is an assay designed to quantitate levels of recombinant human (rhu) GM-CSF in an unknown sample. An anti-GM-CSF murine monoclonal antibody is adsorbed onto a 96-well polystyrene plate overnight. After washing, a standard curve and samples are added to the plate and incubated. The plate is washed to remove any excess unabsorbed rhu-GM-CSF. A polyclonal antibody to rhu-GM-CSF is then added to each well and incubated. The plate is washed to remove any unbound polyclonal antibody and a solution containing donkey anti-sheep IgG antibody conjugated to horseradish peroxidase (HRP) enzyme is added to each well. Following incubation the plate is washed to remove any excess HRP-linked antibody which did not bind to the sheep antibodies present. A developing solution containing the chromogenic substrate for the HRP conjugate is added to the plate. Color development is directly proportional to the amount of HRP-conjugate present. The optical density readings at the correct wavelength give numerical values for each well. These wells can be compared with the standard curve values, permitting quantitation of the levels of rhu-GM-CSF. A monoclonal anti GM-CSF antibody can be obtained from Immunex. A donkey anti-sheep IgG antibody HRP conjugate is obtained from Jackson Immunoresearch Laboratories.

Serum samples were also analyzed for bioactivity by the cell proliferation assay TF-1. A TF1 bioassay is used to detect the presence and amount of human GM-CSF. The TF1 bioassay utilizes a human erythroleukemia cell line, TF1, to detect the presence of huGM-CSF, hu IL-3, or rhu PIXY321 in test samples. These cells are dependent upon huGM-CSF for growth and are maintained in medium supplemented with huGM-CSF. The addition of huGM-CSF, hu IL-3, or rhu PIXY321 to these cells stimulates a dose-dependent proliferation, allowing for quantitation of huGM-CSF, hu IL-3, or rhu PIXY321 in test samples as compared to a standard of known huGM-CSF, hu IL-3, or rhu PIXY321 concentration.

The amount of proliferation is measured by "pulsing" each microwell with tritiated thymidine ($^3$H-TdR) for 4 hours at 37° C. Proliferating TF-1 cells will incorporate ($^3$H-TdR) which is added to the medium into their DNA as they divide. The cells from each well are then harvested onto a glass fiber filter paper which traps the labeled GM-CSF. The amount of $^3$H-TdR trapped on each filter paper is then counted on a beta counter. The number of counts per minute (cpm) for each well is directly proportional to the amount of proliferation by the activated TF-1 cells in response to huGM-CSF, hu IL-3, or ru PIXY321. The resulting counts per minute are directly proportional to the amount of GM-CSF that was stimulating the cell colony.

To determine bioactivity of GM-CSF in the release samples all samples are diluted to 0.2 ng GM-CSF/ml and submitted for analysis. The resulting activities expressed as units/ml are compared to the activity of an untreated stock sample of GM-CSF analyzed simultaneously. In theory, all samples should have approximately 100% activity relative to the stock sample. Between assays control values can range around 20 to 25%, a precision level not unusual with assays based on cell growth.

The percentage of specific activity retained at each time point was determined by dividing the specific activity measured at each time point by the specific activity of stock huGM-CSF of the same lot which had not been incorporated into microspheres.

Figure 2B:
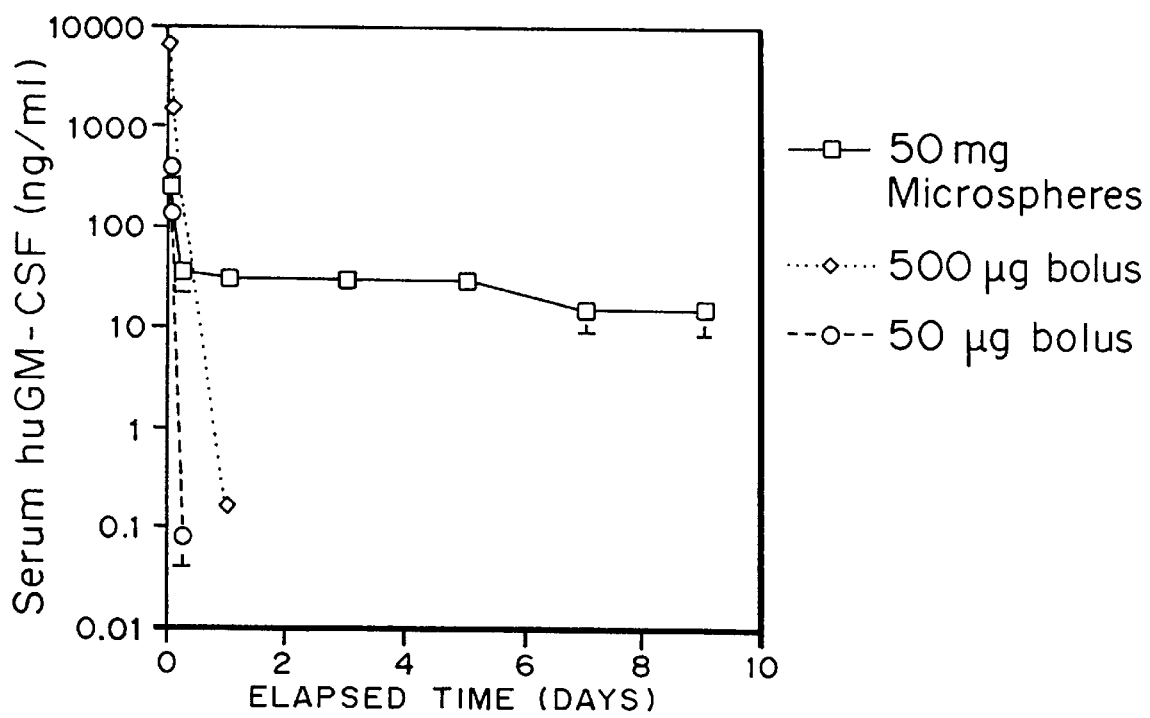
FIG. 2B is a graph of mouse serum GM-CSF levels (ng/ml) over time (days) following microsphere or bolus injections, for 50 mg microspheres, 500 µg bolus, and 50 µg bolus.

Results of the release study are shown in FIG. 2A, which is a graph of the in vitro release kinetics showing release over a period of about ten days. FIG. 2B is a graph of the circulating mouse serum huGM-CSF levels (determined by ELISA) as a function of time. Both the 500 and 50 μg bolus injections were rapidly cleared from mouse serum. Due to the rapid decline of detectable huGM-CSF in mouse serum only a rough estimate of the β elimination half-life could be made ($t_{1/2}\beta$=1.57 hr); however, this estimate agrees closely with previously reported half-lives for huGM-CSF circulating in a mouse model. Levels of serum huGM-CSF in the mice which received microspheres dropped rapidly over the first 6 hours post-injection (from 218 to 35 ng/ml), and then remained relatively constant over the remaining 9 days of the study. Presumably, given the in vitro release profile for this lot of microspheres (approximately 30% release after 9 days) huGM-CSF would have released from the microspheres beyond the 9 day period where the in vivo study was terminated.

Figure 2C:
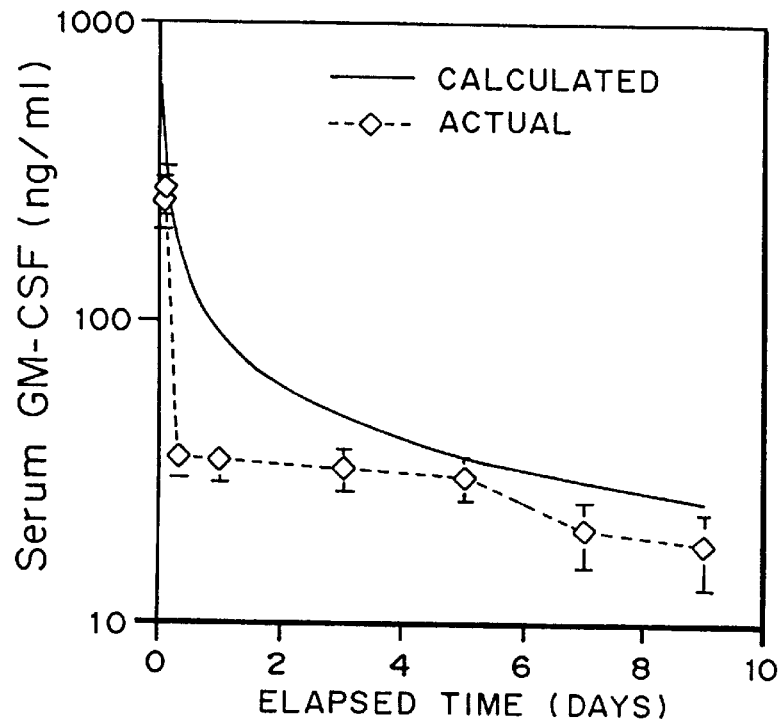
FIG. 2C is a graph of the GM-CSF levels following microsphere injection (diamonds) versus levels calculated from in vitro release rate and experimental half-life (line).

As shown in FIG. 2C, the in vivo release data was compared to the in vitro release data as follows: (1) the in vitro release data was first mathematically modeled to fit a power series; (2) a theoretical in vivo serum huGM-CSF concentration profile was then calculated by taking a mass balance in a single compartment model (i.e. the huGM-CSF concentration in the mouse at any time equals the concentration of huGM-CSF already in the mouse at a previous time point plus the amount of huGM-CSF released from the microspheres over that time period minus the amount of huGM-CSF cleared by normal physiological clearance mechanisms over that same time period). The resulting comparison of serum concentration based on in vitro release and actual in vivo serum huGM-CSF levels is shown in FIG. 2C. As demonstrated in this figure the actual in vivo serum huGM-CSF levels were lower than those predicted by the in vitro release, however, the profiles were similar in shape and remarkably close in values at later time points.

The bioactivity of huGM-CSF released from microspheres in vivo was estimated by TF-1 bioassay. The percent of specific bioactivity varied from a high of 67% at 1 hour and gradually declined to a low of 33% after 9 days.

EXAMPLE 5

Release of Human GM-CSF from Microspheres in a Primate Model.

Microspheres containing huGM-CSF were prepared for in vivo injection in a rhesus monkey model (Lot #9490-168, sample "V4"). Microspheres were first characterized in vitro for protein loading (1.48% wt/wt by amino acid analysis), release kinetics (see FIG. 3A) and bioactivity of released material by TF-1 bioassay (see FIGS. 1B and 3B). Based on the in vitro release profile, microspheres were weighed out such that primates would receive approximately 25 μg/kg/ day for 7 days. Syringes were loaded with microspheres which included an extra 5% for the hold-up volume encountered on injection (50 μl holdup volume for 1 cc tuberculin syringe). Three primates received injections with microspheres containing GM-CSF. One primate received placebo microspheres which did not contain microspheres. The quantity of microspheres injected into each of the primates was 39.4 mg, 35.5 mg, 42.1 mg, and 36.8 mg, for 3.2 kg, 2.9 kg, 3.4 kg, and 3.0 kg animals, respectively.

The injection vehicle for the microspheres was an aqueous solution of low viscosity grade methyl cellulose, containing 3% (wt/wt) methyl cellulose, 0.1% Tween 80, and 4% mannitol.

Figure 3C:
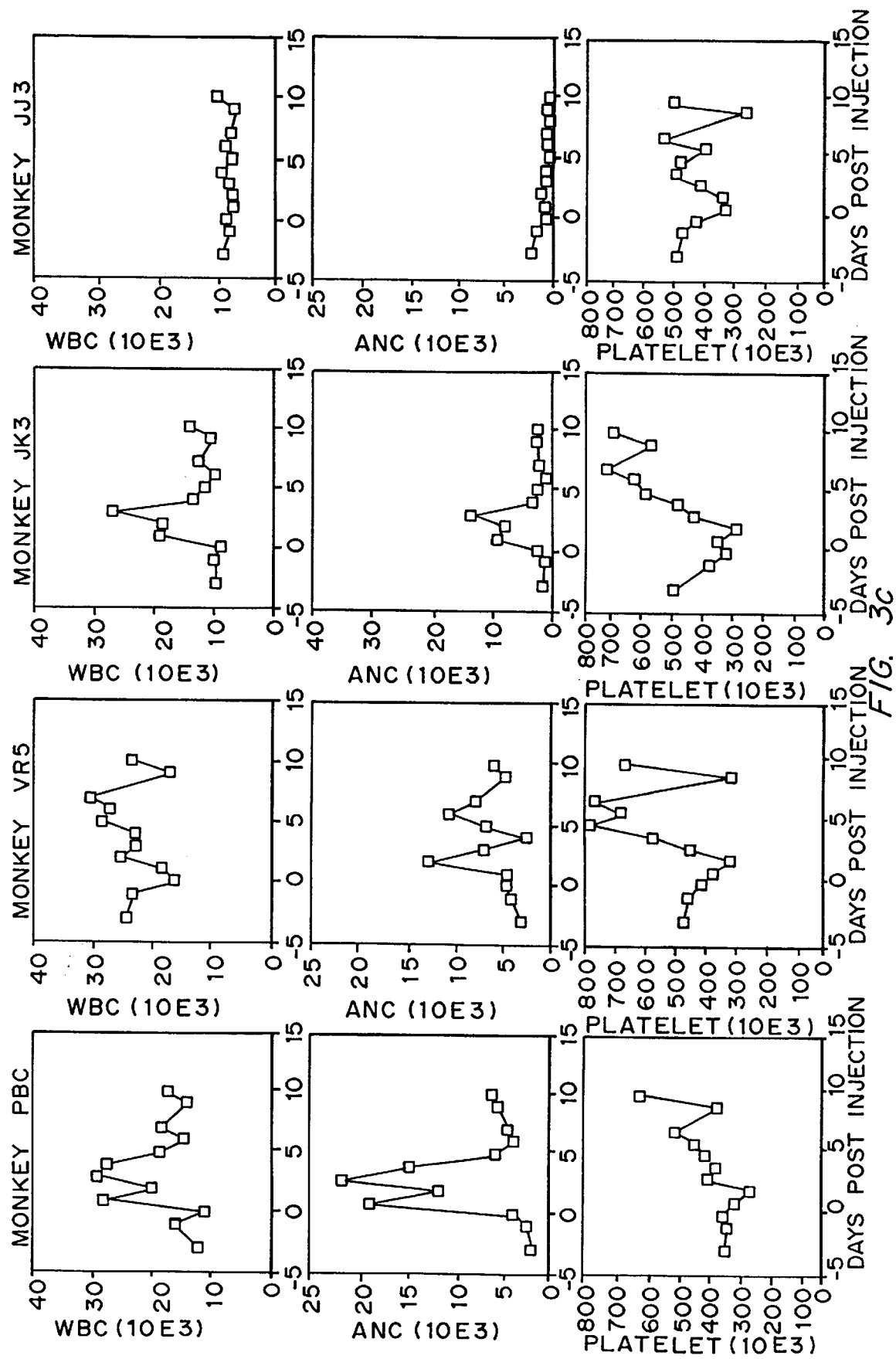
FIG. 3C are graphs of the white blood cell counts (WBC), absolute neutrophil counts (ANC), and platelet counts in primates injected with microspheres containing GM-CSF, as a function of time (days).
Figure 5:
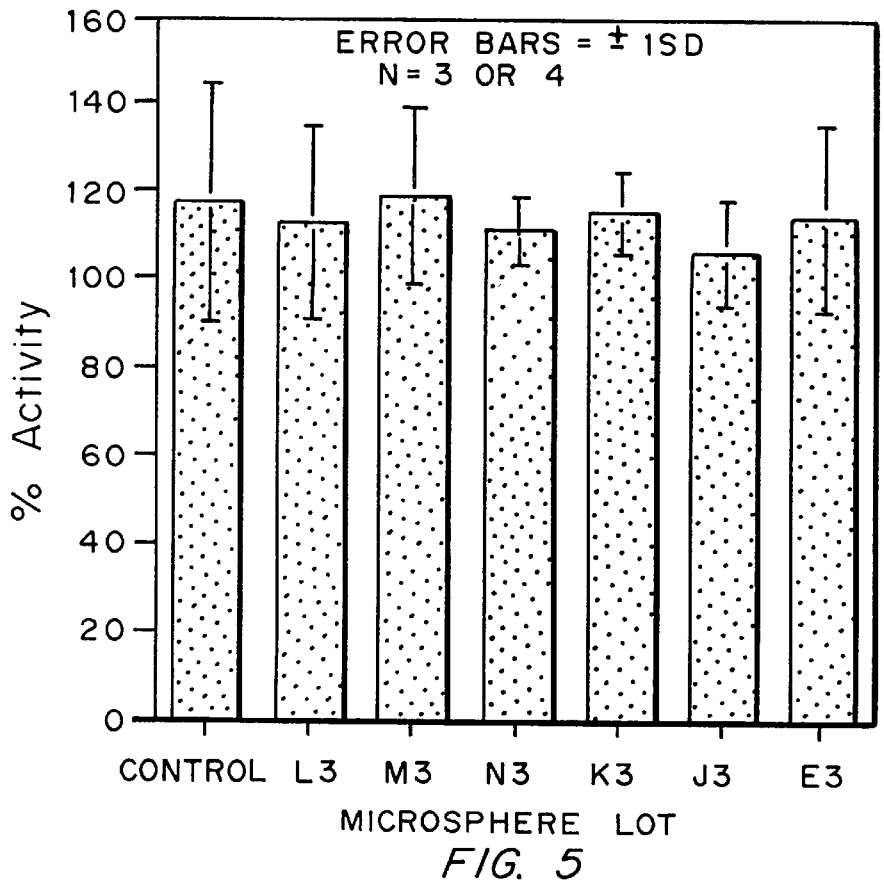
FIG. 5 is a graph of TF-1 cell activity of GM-CSF extracted from PLGA microspheres with acetic acid, graphing percent activity versus microsphere lot.
Figure 6:
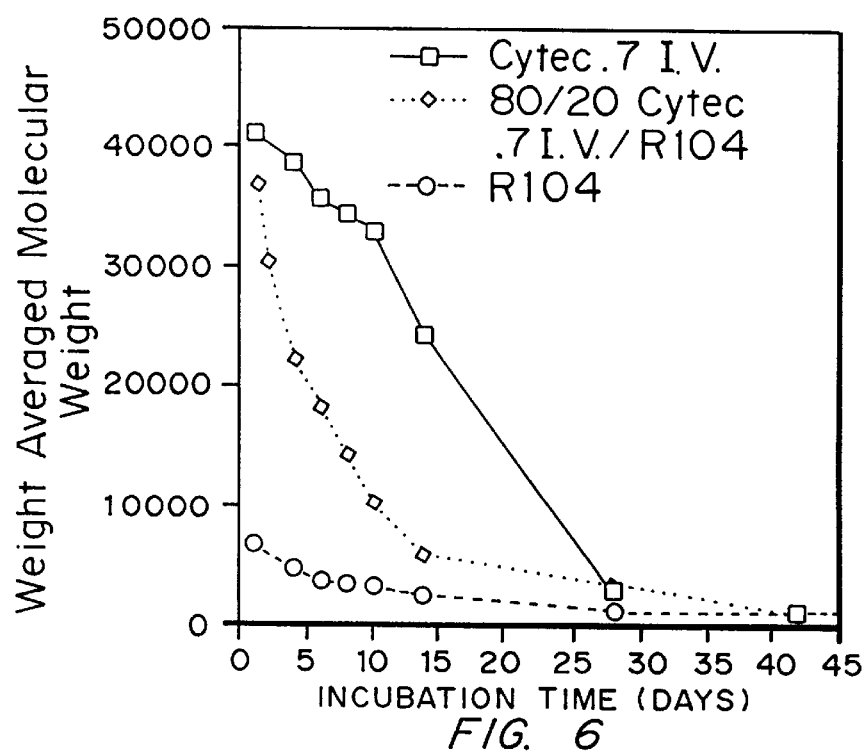
FIG. 6 is a graph of PLGA degradation over time of three types of microspheres prepared from either PLGA (Cytec. 7 I.V.), PLA (R104) or an 80/20 blend of the two polymers, graphing weight average molecular weight over time (days).

Serum samples were collected and analyzed for white blood cell count (WBC), absolute neutrophil count (ANC), and platelet count on days 3 and 1 prior to injection, on the day of injection, and daily following the injection for 10 days. Daily blood cells counts are shown in FIG. 3C.

The WBCs and ANCs were clearly elevated on days 1 through 4 in each of the animals receiving GM-CSF containing microspheres. No changes in blood cell counts were measured for the primate receiving the placebo injection.

This example shows that recombinant human GM-SCF released from PLGA microspheres in vivo, is capable of eliciting a biological response in a non-human primate model.

Highly localized inflammatory response seen in the monkeys was characterized by a significant localized swelling (1–2 cm diameter lump) at the site of injection as a result of recruitment of neutrophils, macrophages, dendritic cells and monocytes.

EXAMPLE 6

Release of GM-CSF From a PLGA Gel.

A 20% solution of PLGA (50:50 lactide glycolide ratio, 0.38 dL/g intrinsic viscosity (I.V.)) was prepared by heating 2 g of PLGA in 8 g of glycerol triacetate (triacetin) at 70° C. for 30 minutes. Lyophilized GM-CSF was added to the PLGA solution at 10 mg/ml and sonicated to complete mixing. Screw top vials (5 ml) were filled with 3 ml PBS and approximately 250 μg of the PLGA/GM-CSF solution (containing approximately 2.5 mg of GM-CSF) was added to each vial by pipetting. The vials were shaken gently at 37° C. for 6 days. The injected solution formed a gel on injection into the PBS. At intervals of 4 hr, 8 hr, 1 day, 3 days, and 6 days, the solutions were removed from the vials and analyzed for GM-CSF content by a BioRad total protein assay.

Figure 4:
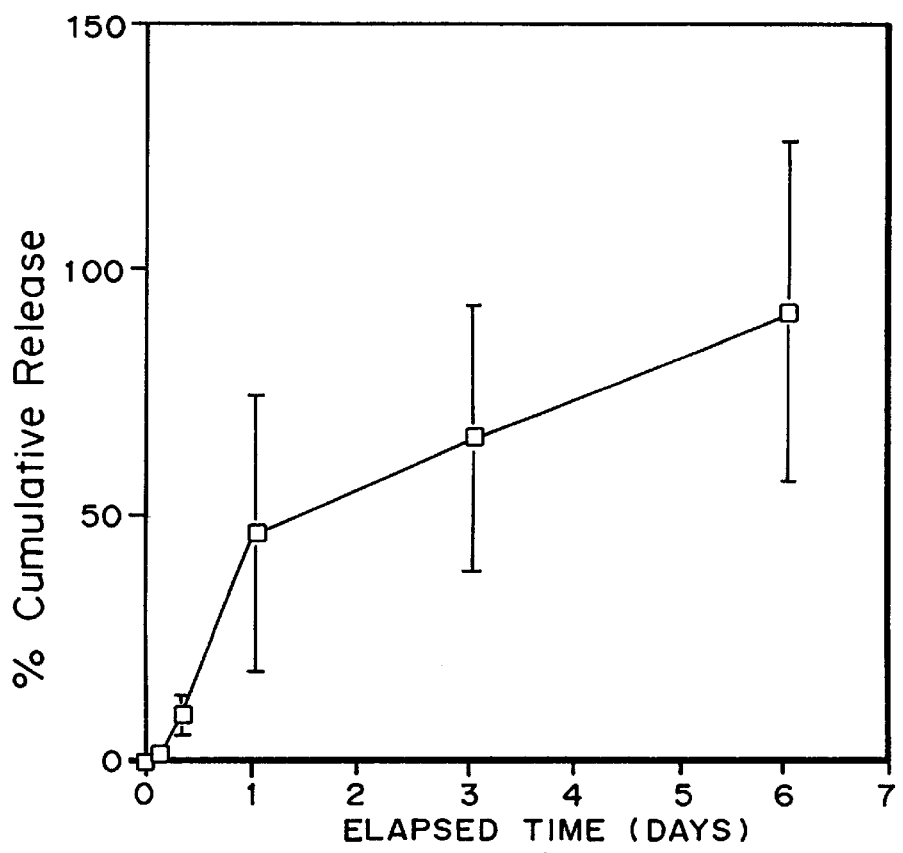
FIG. 4 is a graph of GM-CSF release from a PLGA gel, percent cumulative release over time (days).

The protein release kinetics are shown in FIG. 4 and show first order kinetics over a period of about six days.

EXAMPLE 7

Preparation of Microspheres Using a W/O/W-Methanol Extraction Process. (Lot #14254-138)

The encapsulating polymer was a 70:20:10 mixture of 1) a poly(glycolide-co-d,1 lactide) having a glycolide to lactide ratio of 50:50 and an inherent viscosity of 0.33 dL/g as determined in a 0.1% w/v chloroform solution at 25° C. (polymer I), 2) a poly(L-lactide) with an average molecular weight of 1786 as determined by end group titration (polymer II), and 3) a poly(d,1 lactide) with an average molecular weight of 1938 as determined by end group titration (polymer III). The polymers were reprecipitated before use. The encapsulating polymer solution was prepared by adding 1.40 g of polymer I, 0.40 g of polymer II, and 0.20 g of polymer III to 8.00 g of methylene chloride and stirring the mixture until the polymers dissolved.

A 5% aqueous solution of polyvinyl alcohol (PVA) was prepared by adding 20.00 g of low molecular weight (M.W.= 31,000–50,000, 87–89% hydrolyzed) PVA to 380 g of deionized water, and stirring with heating (to approximately 70° C.) until the PVA is dissolved. The solution was filtered through a 0.2 μm filter after cooling to room temperature.

0.389 ml of a GM-CSF solution (about 87.3 mg/ml in 100 mM tris buffer) was added to 8.50 g of the encapsulating polymer solution in a 30-ml glass beaker, and was homogenized with a 20-mm head at 6000 RPM for 60 seconds to create a water-in-oil (W/O) emulsion.

The above emulsion was added to 400 g of the 5% PVA solution in a stainless steel vessel while it was being stirred with a homogenizer at 6000 RPM using a 20-mm head to create a water-in-oil-in-water (W/O/W) emulsion. Total elapsed time was 1 minute.

The vessel containing the W/O/W emulsion was placed under a mixer equipped with a "high shear disperser" and stirred at 400 RPM. 400 g of methanol was added to the W/O/W emulsion over a 45-minute period to extract the methylene chloride from the microspheres. Stirring was continued for another 45 minutes after the addition of methanol.

Microspheres were collected, dried and particle size distribution was determined as described above.

The sample had a volume median diameter of 24.1 μm, 10% of the microspheres were under 10.8 μm, and 90% of the microspheres were under 42.3 μm.

EXAMPLE 8

Microsphere Preparation using a W/O/W Methanol Extraction Process. (Lot #14254-160)

The encapsulating polymer was a 80:10:10 mixture of 1) a poly(glycolide-co-d,1 lactide) having a glycolide to lactide ratio of 50:50 and an inherent viscosity of 0.33 dL/g as determined in a 0.1% w/v chloroform solution at 25° C. (polymer I), 2) a poly(L-lactide) with an average molecular weight of 1786 as determined by end group titration (polymer II), and 3) a poly(d,1 lactide) with an average molecular weight of 1938 as determined by end group titration (polymer III). The polymers were reprecipitated before use. The encapsulating polymer solution was prepared by adding 1.60 g of polymer I, 0.20 g of polymer II, and 0.20 g of polymer III to 8.00 g of methylene chloride and stirring the mixture until the polymers dissolved.

A 5% aqueous solution of polyvinyl alcohol (PVA) was prepared by adding 20.00 g of low molecular weight (M.W.= 31,000–50,000, 87–89% hydrolyzed) PVA to 380 g of deionized water, and stirring with heating (to approximately 70° C.) until the PVA is dissolved. The solution was filtered through a 0.2 μm filter after cooling to room temperature.

0.389 ml of a GM-CSF solution (about 87.3 mg/ml in 100 mM Tris buffer) were added to 8.50 g of the encapsulating polymer solution in a 30-ml glass beaker, and was homogenized with a 20-mm head at 6000 RPM for 60 seconds to create a water-in-oil (W/O) emulsion.

The above emulsion was added to 400 g of the 5% PVA solution in a stainless steel vessel while it was being stirred with a homogenizer at 6000 RPM using a 20-mm head to create a water-in-oil-in-water (W/O/W) emulsion. Total elapsed time was 1 minute.

The vessel containing the W/O/W emulsion was placed under a mixer equipped with a "high shear disperser" and stirred at 400 RPM. 400g of methanol was then pumped into the W/O/W emulsion at a constant rate over a 5-minute period to extract the methylene chloride from the microspheres. Stirring was continued for another 85 minutes after the addition of methanol.

Microspheres were collected, dried, and particle size distribution was determined as described above.

The sample had a volume median diameter of 26.1 μm, 10% of the microspheres were under 11.6 μm, 90% of the microspheres were under 46.7 μm.

EXAMPLE 9

Preparation of microspheres Lot #14259-100 (Hydrogel)" by a W/O/W methanol extraction process.

The encapsulating polymer was a 67:23:10 block tripolymer of caprolactone, trimethylene carbonate, and polyethylene oxide 8000. 3.27 g of the polymer was mixed with 18.53 g of methylene chloride and stirred until the polymer dissolved.

A 1% aqueous solution of polyvinyl alcohol (PVA) was prepared by adding 11.0 g of low molecular weight (M.W.= 31,000–50,000, 87–89% hydrolyzed) PVA to 1089.00 g of deionized water, and stirring with heating (to approximately 70° C.) until the PVA dissolved. The solution was filtered through a 0.2 μm filter after cooling to room temperature.

0.174 ml of a GM-CSF solution (at 87.1 mg/ml in 100 mM Tris buffer) was added to a 10.00 g portion of the encapsulating polymer solution in a 30-ml glass beaker, and was homogenized with a 20-mm head at 6000 RPM for 60 seconds to create a water-in-oil (W/O) emulsion.

The above emulsion was added to a 500 g portion of the 1% PVA solution in a stainless steel vessel while it was being stirred with a homogenizer at 6000 RPM using a 20-mm head to create a water-in-oil-in-water (W/O/W) emulsion. Total elapsed time was 1 minute.

The vessel containing the W/O/W emulsion was placed under a mixer equipped with a "high shear disperser" and stirred at 400 RPM. 500 g of methanol was pumped into the W/O/W emulsion over a 5-minute period to extract the methylene chloride from the microspheres. Stirring was continued for another 55 minutes after the addition of methanol.

Microspheres were collected, dried and particle size distribution was determined with a Malvern 2600 Particle Sizer. Approximately 50 mg of microspheres was suspended in about 10 ml of methanol, and was sonicated for 2 minutes to fully disperse the microspheres. A few drops of this suspension were then added to the optical cell which contained methanol. The particle size distribution was then measured. The sample had a volume median diameter of 68.3 μm, 10% of the microspheres were under 14.3 μm and 90% of the microspheres were under 177.3 μm.

EXAMPLE 10

Extraction of GM-CSF from Microspheres for In Vitro Determination of Bioactivity.

This method of extracting the protein from the microspheres is both quantitative and nondestructive and therefore can be used to determine the integrity of the incorporated protein. Approximately 20 mg microspheres (Lots L3, M3, N3, K3, J3, and E3) prepared by the phase separation method described in Example 1 were weighed into a 2 ml Eppendorf tube. 500 μl of glacial acetic acid was then added and the tubes were capped and periodically vortexed to completely dissolve the microspheres. 500 μl methylene chloride was then added and the tubes were capped and vortexed periodically for about 5 minutes. Finally 500 μl PBS were added and, again, the tubes were capped and vortexed continually for about 2 minutes. The capped tubes were next centrifuged in a microfuge at high speed for 2 minutes to facilitate clean separation of the aqueous and organic solvent phases. The absorbance of 280 nm of the upper aqueous layer (1 ml) containing the GM-CSF was determined and the concentration of GM-CSF in mg/ml was calculated by dividing the absorbance by the extinction coefficient of 1.08. The samples were then submitted for TF1 bioassay to determine the bioactivity of the GM-CSF.

FIG. 5 shows the percent bioactivity of the GM-CSF extracted from the microspheres. The control is an aqueous GM-CSF sample that has gone through the same extraction process. These results indicate that the GM-CSF extracted from the microspheres has retained complete bioactivity.8

EXAMPLE 11

Preparation of PLGA microspheres and PLGA degradation profiles.

Microspheres containing 100% Cytec, 0.7 dL/g intrinsic viscosity (I.V.) PLGA, 100% R104 PLA, and an 80:20 mixture of the PLGA:PLA were prepared by the silicone oil hardening process. Samples of each of these microspheres were incubated at 37° C. in PBS for periods of 1, 2, 4, 6, 8, 10, 14, 28, 42, and 56 days. Following incubation the microspheres were dissolved in tetrahydrofuran (THF) making 1 to 2% solutions (microsphere wt/THF volume). The samples were then analyzed by gel permeation chromatography (GPC) using Waters HPLC system with a styragel HR-4E column (Waters) which was maintained at 30° C. throughout the GPC run. Polystyrene narrow molecular weight range standards were used to calibrate the column. Weight and number average molecular weights of the degraded PLGA polymers were determined with Millenium GPC software (Waters). FIG. 6 below illustrates the weight average molecular weights of each microsphere formulation as a function of incubation time. Note that the degradation of microspheres prepared from the 100% Cytec 0.7 I.V PLGA was incomplete over a 14 day incubation period whereas the 80:20 mixture of Cytec 0.7 I.V./R104 was essentially degraded. In this example the R104 PLA acted as a degradation enhancer for the microspheres.

Modifications and variations of the compositions and methods for manufacture and use described herein will be obvious to those skilled in the art from the foregoing description. Such modifications and variations are intended to come within the scope of the appended claims.

We claim:

1. A hydrogel comprising GM-CSF dispersed therein, wherein the hydrogel absorbs water in an amount up to 90% of the final weight of the hydrated hydrogel.

2. The hydrogel of claim 1 wherein the hydrogel is formed into microparticles.

3. The hydrogel of claim 1 wherein the hydrogel is formed from a polymer selected from the group consisting of ionically crosslinkable polysaccharides, synthetic biodegradable, biocompatible polymers, and proteins.

4. The hydrogel of claim 3 wherein the polymer is selected from the group consisting of alginate, polyphosphazenes, polyacrylates, polyethylene oxide-polypropylene glycol block copolymers, and hyaluronic acid.

5. The hydrogel of claim 1 wherein the hydrogel is complexed and stabilized with polylons.

6. The hydrogel of claim 1 wherein the hydrogel further comprises a chemoattractant for white blood cells.

7. The hydrogel of claim 1 wherein the hydrogel further comprises a pharmaceutically acceptable carrier for administration to a patient in need thereof.

8. A method for treating a patient comprising administering an effective amount of GM-CSF in combination with a biocompatible synthetic polymer, which is a chemoattractant, wherein the combination is in a pharmaceutically acceptable carrier for administration to a patient in need thereof.

9. The method of claim 8 wherein the GM-CSF is administered in combination with an antigen.

10. A method for administering GM-CSF to a patient in need thereof comprising administering to the patient an effective amount of GM-CSF dispersed in a synthetic polymeric hydrogel which absorbs up to 90% of the final weight of water.

11. The method of claim 10 wherein the hydrogel is formed into microparticles.

12. The method of claim 10 wherein the hydrogel is formed from a polymer selected from the group consisting of ionically crosslinkable polysaccharides, synthetic biodegradable, biocompatible polymers, and proteins.

13. The method of claim 12 wherein the polymer is selected from the group consisting of alginate, polyphosphazenes, polyacrylates, polyethylene oxide-polypropylene glycol block copolymers, and hyaluronic acid.

14. The method of claim 10 wherein the hydrogel is complexed and stabilized with polyions.

15. The hydrogel of claim 1 wherein the hydrogel further comprises a compound selected from the group of a degradation enhancer, a stabilizer, a solubilizer, and a buffering agent.

16. The hydrogel of claim 1 wherein the hydrogel is bioadhesive.

17. The hydrogel of claim 7 wherein the pharmaceutically acceptable carrier further comprises an immunostimulant.

18. The method of claim 11 wherein the hydrogel is administered by injection.

19. The method of claim 10 wherein the hydrogel is administered orally.

20. The method of claim 12 wherein the hydrogel is administered topically.

21. The method of claim 8 wherein the pharmaceutically acceptable carrier comprises an immunostimulant.

22. The method of claim 10 wherein the hydrogel further comprises a compound selected from the group consisting of a degradation enhancer, a stabilizer, a solubilizer, and a buffering agent.

23. The hydrogel of claim 17 wherein the hydrogel further comprises an antigen.

* * * * *

UNITED STATES PATENT AND TRADEMARK OFFICE
CERTIFICATE OF CORRECTION

PATENT NO.   : 6,120,807
DATED        : September 19, 2000
INVENTOR(S)  : Gombotz et al.

It is certified that error appears in the above-identified patent and that said Letters Patent is hereby corrected as shown below:

Title page,
Item [57], ABSTRACT,
Line 13, "hare" should read -- have --.

Column 23,
Line 5, "polylons" should read -- polyions --.

Column 24,
Line 19, "claim 12" should read -- claim 10 --.

Signed and Sealed this

Eighth Day of October, 2002

*Attest:*

*Attesting Officer*

JAMES E. ROGAN
*Director of the United States Patent and Trademark Office*